US009279747B2

(12) United States Patent
Young et al.

(10) Patent No.: US 9,279,747 B2
(45) Date of Patent: *Mar. 8, 2016

(54) COLLECTION DEVICE AND MATERIAL (71) Applicant: PURITAN MEDICAL PRODUCTS COMPANY, LLC, Guilford, ME (US)

(72) Inventors: Terry Young, Guilford, ME (US); Timothy Templet, Guilford, ME (US); Paul Dube, Guilford, ME (US); Todd Dixon, Guilford, ME (US); Armand F. Lewis, Mattapoisett, MA (US); Yong K. Kim, Dartmouth, MA (US)

(73) Assignee: PURITAN MEDICAL PRODUCTS COMPANY, LLC, Guilford, ME (US)

( * ) Notice: Subject to any disclaimer, the term of this patent is extended or adjusted under 35 U.S.C. 154(b) by 288 days.

This patent is subject to a terminal disclaimer.

(21) Appl. No.: 13/625,195

(22) Filed: Sep. 24, 2012

(65) Prior Publication Data
US 2013/0096463 A1 Apr. 18, 2013

Related U.S. Application Data (63) Continuation of application No. 12/849,343, filed on Aug. 3, 2010, now Pat. No. 8,334,134.

(60) Provisional application No. 61/326,466, filed on Apr. 21, 2010.

(51) Int. Cl.
*C12M 1/26* (2006.01)
*G01N 1/10* (2006.01)
(Continued)

(52) U.S. Cl.
CPC .............. *G01N 1/10* (2013.01); *A61B 10/0045* (2013.01); *B32B 37/16* (2013.01); *D01D 5/36* (2013.01);
(Continued)

(58) Field of Classification Search
CPC .......... A61B 10/0045; A61B 10/0051; A61B 10/007; A61B 2010/0067; A61B 10/0047; A61B 10/0216; G01N 1/10; D01D 5/36; D01F 8/12; D01F 8/14; B32B 37/16
USPC ............ 15/83, 221, 209.1, 210.1, 229.3, 446; 73/855, 856, 159, 160; 435/29, 309.1; 156/221; 604/1, 2, 3
See application file for complete search history.

(56) References Cited

U.S. PATENT DOCUMENTS 3,163,160 A 12/1964 Cohen
3,900,651 A 8/1975 Hoppe et al.
(Continued)

FOREIGN PATENT DOCUMENTS

EP 0223745 5/1987
EP 0244156 B1 4/1990
(Continued)

OTHER PUBLICATIONS

Grafe et al, "Polymeric Nanofibers and Nanofiber Webs: A New Class of Nonwovens", INTC 2002: International Nonwovens Technical Conference (Joint INDA—TAPPI Conference), Atlanta, Georgia, Sep. 24-26, 2002 (13 pages).

(Continued)

*Primary Examiner* — Michael Hobbs
(74) *Attorney, Agent, or Firm* — Nixon & Vanderhye P.C.

(57) ABSTRACT

Swabs, and materials of the present disclosure, and methods of making same, include randomly arranged sea-island bicomponent fibers which have randomly splayed terminal ends.

22 Claims, 4 Drawing Sheets (51) Int. Cl.
*A61B 10/00* (2006.01)
*D01D 5/36* (2006.01)
*D01F 8/12* (2006.01)
*D01F 8/14* (2006.01)
*B32B 37/16* (2006.01)
*A61B 10/02* (2006.01)

(52) U.S. Cl.
CPC .. *D01F 8/12* (2013.01); *D01F 8/14* (2013.01); *A61B 10/007* (2013.01); *A61B 10/0051* (2013.01); *A61B 2010/0067* (2013.01); *A61B 2010/0074* (2013.01); *A61B 2010/0216* (2013.01); *Y10T 156/10* (2015.01); *Y10T 156/1043* (2015.01); *Y10T 156/1089* (2015.01)

(56) References Cited

U.S. PATENT DOCUMENTS

| | | |
|---|---|---|
| 4,030,978 A | 6/1977 | Abramson |
| 4,039,934 A | 8/1977 | Ostashko |
| 4,059,404 A | 11/1977 | Schuster et al. |
| 4,421,809 A | 12/1983 | Bish |
| 4,707,450 A | 11/1987 | Nason |
| 4,719,181 A | 1/1988 | Schobel |
| 4,749,655 A | 6/1988 | Corasaniti |
| 4,767,398 A | 8/1988 | Blasius, Jr. |
| 4,820,259 A | 4/1989 | Stevens |
| 4,861,343 A | 8/1989 | Neunzig |
| 4,877,037 A | 10/1989 | Ko |
| 5,009,846 A | 4/1991 | Gavet |
| 5,163,441 A | 11/1992 | Monthony |
| 5,623,941 A | 4/1997 | Hedberg |
| 5,738,643 A | 4/1998 | Stedic |
| 5,762,494 A | 6/1998 | Archambault |
| 5,944,519 A | 8/1999 | Griffiths |
| 6,232,567 B1 | 5/2001 | Bonino |
| 6,352,513 B1 | 3/2002 | Anderson |
| 6,450,810 B1 | 9/2002 | Fischer |
| 6,835,865 B2 | 12/2004 | Quincy, III |
| 7,022,289 B1 | 4/2006 | Schlein |
| 8,114,027 B2 | 2/2012 | Triva |
| 2002/0001539 A1 | 1/2002 | DiCesare et al. |
| 2002/0197738 A1 | 12/2002 | Matsumoto et al. |
| 2003/0073932 A1 | 4/2003 | Varey |
| 2003/0108846 A1 | 6/2003 | Hoertsch |
| 2003/0120180 A1 | 6/2003 | Kaylor et al. |
| 2003/0203695 A1 | 10/2003 | Polanco et al. |
| 2004/0014063 A1 | 1/2004 | Batteux |
| 2004/0158188 A1 | 8/2004 | Kauffman |
| 2004/0197730 A1 | 10/2004 | Rowe |
| 2005/0181517 A1 | 8/2005 | Chandler et al. |
| 2006/0115805 A1 | 6/2006 | Hansen et al. |
| 2007/0208274 A1 | 9/2007 | Ostrowski et al. |
| 2007/0264520 A1 | 11/2007 | Wood et al. |
| 2007/0282223 A1 | 12/2007 | Larkin |
| 2008/0125687 A1 | 5/2008 | Flick et al. |
| 2008/0208100 A1 | 8/2008 | Wolff |
| 2009/0030341 A1 | 1/2009 | Kshirsagar et al. |
| 2010/0029158 A1 | 2/2010 | Kamiyama et al. |
| 2010/0068516 A1 | 3/2010 | Yoon et al. |
| 2010/0075143 A1 | 3/2010 | Hashimoto et al. |
| 2010/0274155 A1* | 10/2010 | Battrell et al. .............. 600/572 |
| 2011/0028861 A1 | 2/2011 | Triva |
| 2011/0104430 A1 | 5/2011 | Mehrabi et al. |
| 2011/0262951 A1 | 10/2011 | Young et al. |
| 2011/0262952 A1 | 10/2011 | Young et al. |

FOREIGN PATENT DOCUMENTS

| | | |
|---|---|---|
| EP | 0 643 131 A2 | 3/1995 |
| EP | 0707836 A2 | 4/1996 |
| JP | 2004-130209 | 4/2004 |
| WO | WO89/10724 | 11/1989 |
| WO | WO9212863 | 8/1992 |
| WO | WO0054024 | 9/2000 |
| WO | WO 02/42528 A1 | 5/2002 |
| WO | WO 02/42529 A1 | 5/2002 |
| WO | WO 02/088438 A1 | 11/2002 |
| WO | WO2004/086979 A1 | 10/2004 |
| WO | WO 2004/086979 A1 | 10/2004 |
| WO | WO2004086979 | 10/2004 |
| WO | WO2005/013759 A1 | 2/2005 |
| WO | WO2005/110316 A1 | 11/2005 |
| WO | WO2007/075412 A2 | 7/2007 |
| WO | WO2007/075412 A3 | 7/2007 |
| WO | WO2008/131033 A1 | 10/2008 |
| WO | WO 2009/018473 A1 | 2/2009 |
| WO | WO2009/018607 A1 | 2/2009 |
| WO | WO2009/134509 A2 | 11/2009 |
| WO | WO2009/136892 A1 | 11/2009 |
| WO | WO2009/140356 A1 | 11/2009 |

OTHER PUBLICATIONS

Ndaro et al, "Splitting of Islands-in-the-Sea Fibers (PA6/COPET) During Hydroentangling of Nonwovens", Journal of Engineered Fibers and Fabrics, vol. 2, Issue 4, 2007.
Fedorova, N., "Investigation of the Utility of Islands-In-The-Sea Bicomponent Fiber Technology in the Spunbond Process" A dissertation submitted to the Graduate Faculty of North Carolina State University, In partial fulfillment of the requirements for the Degree of Doctor of Philosophy, Raleigh, NC 2006.
"Flock and flocking—understanding the process" printed from http://docucomp.archive.org on Jul. 22, 2008 (5 pages).
"Understanding the flocking process" printed from http://web.archive.org on Jul. 22, 2008 (7 pages).
European Search Report dated Jul. 22, 2011, issued in connection with EP 10 25 1388.4.
European Search Report dated Jul. 25, 2011, issued in connection with EP 10 25 1389.2.
International Search Report and Written Opinion dated Jun. 15, 2011, issued in connection with PCT/US2010/002155.
International Search Report and Written Opinion dated Jun. 15, 2011, issued in connection with PCT/US2010/002154.
Sahbaee Bagherzadeh, "Abrasion and Pilling Resistance of Nonwoven Fabrics Made from Bicomponent Fibers", Master dissertation, North Caroline State University, Releigh, NC, USA, 2007.
Certified English translation of JP 2004-130209 (Apr. 30, 2004) and certification.
U.S. Patent Office File History of U.S. Appl. No. 10/543,873 titled "Swab for Collecting Biological Specimens" printed from U.S. Patent Office Image File Wrapper on May 26, 2011.
US Patent Office, Office Actions/Communications dated Mar. 4, 2011, Nov. 29, 2010, Jul. 19, 2010, Jul. 15, 2010, Mar. 23, 2010, Dec. 14, 2009, Aug. 14, 2009, Apr. 14, 2008, Mar. 17, 2008, in U.S. Appl. No. 10/543,873, titled "Swab for Collecting Biological Specimens". Submissions by applicants dated Nov. 30, 2010, Sep. 23, 2010, Aug. 23, 2010, Jun. 8, 2010, Dec. 17, 2009, Nov. 16, 2009, May 27, 2009, May 8, 2007,Jul. 28, 2005 in U.S. Appl. No. 10/543,873, titled "Swab for Collecting Biological Specimens".
GB406850(A) Mislowitzer, (abstract) published Mar. 8, 1934 "Devices for dispatching "Abstriche" Blood Samples and the Like for Bacteriological and Diagnostic Purposes".
Pages 212 and 147 of Merriam Webster's Collegiate Dictionary, Tenth Edition (1994) Merriam-Webster Incorporated.
Declaration of Daniele Triva Under 37 CFR §1.132 dated Nov. 10, 2009, filed in U.S. Appl. No. 10/543,873, bearing USPTO date stamp of Nov. 18, 2009.
Castriclano et al "Increased Rates of respiratory Viral [RV] Infections Using Flocked Swabs and UTM-RT" 17th European Congress of Clinical Microbiology and Infectious Diseases, Munich, Germany, Mar. 31-Apr. 3, 2007 (1 page), as mentioned in Declaration of Daniele Triva Under 37 CFR §1.132 dated Nov. 10, 2009, filed in U.S. Appl. No. 10/543,873, bearing USPTO date stamp of Nov. 18, 2009.
US Patent Office, Office Actions/Communications dated Mar. 4, 2011, Nov. 29, 2010, Aug. 31, 2010, May 22, 2009, Jan. 27, 2009, (56) References Cited

OTHER PUBLICATIONS

Oct. 30, 2008, Feb. 28, 2008, Nov. 30, 2007, Aug. 27, 2007, May 31, 2007, in U.S. Appl. No. 10/543,873, titled "Swab for Collecting Biological Specimens", Triva.

Submissions by applicants dated Nov. 30, 2010, May 27, 2009 Sep. 23, 2010, Nov. 10, 2008, Jul. 1, 2008, Mar. 4, 2008, Feb. 25, 2008, Mar. 21, 2008, Aug. 28, 2007, in U.S. Appl. No. 10/543,873, titled "Swab for Collecting Biological Specimens".

JP2004000587 "Applicator Covered With Flocking of Different Kinds of Fibers Especially for Cosmetics or the Like", Published Jan. 8, 2004, Gueret (English Abstract).

JP200342591(A) "Specimen Collection Appliance Set", Published Dec. 12, 2000, Arai (English Abstract).

JP2002067201(A) "Flocked Material and Decorative Sheet as well as its Manufacturing Method", Published Mar. 5, 2002, Obata (English Abstract).

JP05-027671,U machine translation printed Sep. 21, 2010, publication dated Apr. 9, 1993.

International Preliminary Report on Patentability mailed in PCT/EP2004/003392 completed Feb. 22, 2005 by Tragoustis of European Patent Office.

CN201131761(Y) "Cervices Sampler", Jinhua Zhang (Abstract), Publication Date: Oct. 15, 2008.

Abu-Diab et al. "comparison between Pernasal Flocked Swabs and Nasopharyngeal Aspirates for Detection of Common Respiratory Viruses in Samples from Children" Journal of Clinical Microbiology, Jul. 2008, pp. 2414-2417, vol. 46., No. 7.

Fiebelkorn et al "Performance of Rapid EIA, DFA, RMix, and Conventional Culture for Detection of Respiratory Viruses in Pediatric vs. Adult Populations" paper M-35, UT Health Science Center, contained in U.S. Appl. No. 10/543,873, titled "Swab for Collecting Biological Specimens", Triva, Clinical Virology Symposium—CVS 2008, May 5, 2008.

Walsh et al "Comparison of RSV RNA Recovery by PCR Using Different Methods of Specimen Preservation" Kern Medical Center, contained in U.S. Appl. No. 10/543,873, titled "Swab for Collecting Biological Specimens", Triva, American College of Emergency Physicians (ACEP) Scientific Assembly 2007, Washington State Convention Center, Seattle, WA, Oct. 8-11, 2007.

Walsh et al "Comparison of Three Nasal Collection Specimen Methods for the Detection of Pediatric Respiratory Infectious Disease" Medical Diagnostic Laboratories, contained in U.S. Appl. No. 10/543,873, titled "Swab for Collecting Biological Specimens", Triva, Association of Molecular Pathlogy (AMP) $13^{th}$ Annual Meeting, Nov. 7-10, 2007.

Biggs et al "Prevalence of Pediatric Respiratory Infections in a Suburban Philadelphia Hospital" $23^{rd}$ Annual Clinical Virology Symposium and Annual Meeting of the Pan American Society, Clearwater Beach, FL, Apr. 30, 2007.

Silbert "Comparative Study of the Ability of a New and Novel Swab transport System to Maintain Viability of Clinically Important Aerobes at Room and Refrigerator Temperatures" C-100, ASM $106^{th}$ General Convention —Orlando, Florida, May 2006.

Jones "A new concept for transporting clinical material on flocked swabs in liquid amies medium" C-107, ASM $106^{th}$ General Convention—Orlando, Florida—May 22-24, 2006.

Van Horn et al "Evaluation and Comparison of Three Swab Collection and Transport Systems Tested by the CLSI M40-A Method" C-108, ASM $106^{th}$ General Convention—Orlando, Florida—May 22-24, 2006.

Sarina et al "Comparative Evaluation of Three Transport Swabs Potential to Maintain Viability of Clinically Important Aerobic and Anaerobic Organisms" C-362, ASM $106^{th}$ General Convention—Orlando, Florida—May 22-24, 2006.

Condon et al "Comparison of the Copan Transystem Swab and the Copan ESwab for the Preservation and Recovery of Fastidious Bacteria" ASM 2007, Abstract C-363.

Biggs et al "Evaluation of ESwab a New Multipurpose Liquid Swab Transport System for Aerobic and Anaerobic Bacteriology" ASM 2007, Abstract C-365.

Coleman "Comparative Study of the Ability of New Copan ESwab (Liquid Amies Transport System) with Another Swab Transport System for Maintaining Viability of Clinically Important Aerobic Bacteria" contained in U.S. Appl. No. 10/543,873 file history, titled "Swab for Collecting Biological Specimens", Triva, ASM 2007, American Society of Microbiology, Toronto, Canada—May 21-25, 2007.

Silbert et al "Complete MRSA Nasal Screening Using a Single, New and Novel Swab System" C-368, ASM $107^{th}$ General Convention—Toronto CA, May 2007.

DeFields et al, "P-19: Evaluation of Flocked Nylon Swabs (Copan ESwab) vs Rayon Fibre Swabs (Copan Venturi Transystem) for Bacterial Culture" contained in U.S. Appl. No. 10/543,873 file history, titled "Swab for Collecting Biological Specimens", Triva, The Canadian Journal of Infectious Diseases & Medical Microbiology, Jan./Feb. 2007, vol. 18, No. 1.

Magauran et al "Nylon Flocked Swabs Versus Rayon Swabs for Respiratory Viral Recovery of Pediatric Nasopharyngeal Specimens: Which is Better?", contained in U.S. Appl. No. 10/543,873 file history, titled "Swab for Collecting Biological Specimens", Triva, $23^{rd}$ Annual Clinical Virology Symposium—Clearwater Beach, Florida USA, Apr. 29-May 2, 2007.

Biggs et al "Benefirs of Using Copan's Universal Transport Medium (UTM) and Flocked Swab with the Binax Now Flu A/B Test System for Reflex Testing", contained in U.S. Appl. No. 10/543,873 file history, titled "Swab for Collecting Biological Specimens", Triva, $23^{rd}$ Annual Clinical Virology Symposium—Clearwater Beach, Florida USA, Apr. 29-May 2, 2007.

Class et al "Comparison of Flocked Swabs Versus Mattress Swabs and Nasal Aspirates for the Collection of Nasopharyngeal Samples", contained in U.S. Appl. No. 10/543,873 file history, titled "Swab for Collecting Biological Specimens", Triva, $23^{rd}$ Annual Clinical Virology Symposium—Clearwater Beach, Florida USA, Apr. 29-May 2, 2007.

Ng et al "Comparison of Nasopharyngeal (NP) Swabs Collected with Pernasal Flocked Swabs Versus NP Swabs Collected with Traditional Twisted Wire Fiber Minitip for the Detection of Respiratory Viruses Using Simulfluor DFA", contained in U.S. Appl. No. 10/543,873 file history, titled "Swab for Collecting Biological Specimens", Triva, Clinical Virology Symposium—CVS 2008, May 5, 2008.

Allen et al "Comparison of a Mid-Turbinate Flocked Swab to a Nasopharyngeal Flocked Swab for Respiratory Virus Detection in Children" M-28, $24^{th}$ Annual Clinical Virology Symposium and Annual Meeting of the Pan American Society for Clinical Virology, Daytona Beach, Florida, Apr. 27-30, 2008.

Bocher et al, "The search and destroy strategy does prevent spread and long term carriage of MRSA; Results from household screening following an ST22 (E-MRSA 15) outbreak", P654, contained in U.S. Appl. No. 10/543,873 file history, titled "Swab for Collecting Biological Specimens", Triva, European Congress of Clinical Microbiology and Infectious Diseases—ECCMID 2008, Apr. 19-22, 2008.

Christine Biggs, "Copan's Transport Medium (UTM RT) and Flocked Swab for RSV/Flu Collection" P40, contained in U.S. Appl. No. 10/543,873 file history, titled "Swab for Collecting Biological Specimens", Triva, European Society for Clinical Virology, Birmingham, UK—Sep. 3, 2008.

Vare et al "Comparison of Nylon Swabs Versus Cotton Swabs for the Diagnosis of Herpes Simplex Virus", contained in U.S. Appl. No. 10/543,873 file history, titled "Swab for Collecting Biological Specimens", Triva, ESCV 2008, Clinical Virology Annual Meeting Saariselka, Lapland, Finland, Mar. 12-15, 2008.

Waris et al "Comprison of different sampling types for the detection of rhinovirus infections using quantitative RT-PCR", contained in U.S Appl. No. 10/543,873 file history, titled "Swab for Collecting Biological Specimens", Triva, ESCV 2008, Clinical Virology Annual Meeting Saariselka, Lapland, Finland, Mach 12-15, 2008.

Krech et a; "Sampling of Human Papilloma Viruses and Chlamydia trachomatis: Novel Flocked Swabs Increase Detection Rates significantly", contained in U.S. Appl. No. 10/543,873 file history, titled "Swab for Collecting Biological Specimens", Triva, ESCV 2008, Clinical Virology Annual Meeting Saariselka, Lapland, Finland, Mar. 12-15, 2008.

(56) References Cited

OTHER PUBLICATIONS

Biggs et al "Evaluation . . . For the Collection of Respiratory Specimens for Cell Culture", contained in U.S. Appl. No. 10/543,873 file history, titled "Swab for Collecting Biological Specimens", Triva, Clinical Virology Symposium—CVS 2008.

Walsh et al "Comparison of Respiratory Virus Detection Rates for Infants and Toddlers by Use of Flocked Swabs, Saline Aspirates and Saline Aspirates Mixed in Universal transport Medium for Room Temperature Storage and Shipping", Journal of Clinical Microbiology, vol. 46, No. 7, pp. 2374-2376, Jul. 2008.

Daley et al "Comparison of Flocked and Rayon Swabs for Collection of Respiratory Epithelial Cells from Uninfected Volunteers and Symptomatic Patients" Journal of Clinical Microbiology, vol. 44, No. 6, pp. 2265-2267, Jun. 2006.

Chan et al :Comparison of nasopharyngeal flocked swabs and aspirates for rapid diagnosis of respiratory viruses in children Journal of Clinical Virology "Article in Press" 2008.

Van Horn "Comparison of the Copan ESwab System with Two Amies Agar Swab Transport Systems for Maintenance of Microorganism Viability" Journal of Clinical Microbiology, vol. 46., No. 5, pp. 1655-1658, May 2008.

Richardson et al "Lowered Sample Rejection Rate for Rapid Direct Detection of respiratory Viruses in Children by Use of a Flocked Swab and Nasopharyngeal Sampling" M25, contained in U.S. Appl. No. 10/543,873 file history, titled "Swab for Collecting Biological Specimens", Triva, $23^{rd}$ Annual Clinical Virology Symposium—Clearwater Beach, Florida USA, Apr. 29-May 2, 2007.

Mueller et al "Recovery of Respiratory Viruses: Collected by Flocked Swabs Compared to Those Collected by Nasal Aspiration" M-34, contained in U.S. Appl. No. 10/543,873 file history, titled "Swab for Collecting Biological Specimens", Triva, Clinical Virology Symposium—CVS 2008, May 8, 2008.

DeByle et al, "Comparison of Nasopharyngeal Wash and Nasopharyngeal Flocked Swab Samples for Polymerase Chain Reaction (PCR) Detection of Viruses Causing Lower Respiratory Tract Infections in Children", $23^{rd}$ Annual Clinical Virology Symposium—Clearwater Beach, Florida USA, Apr. 29-May 2, 2007.

Nugent et al, "Evaluation of the Physical and Diagnostic Nature of Swabs", $23^{rd}$ Annual Clinical Virology Symposium—Clearwater Beach, Florida USA, Apr. 29-May 2, 2007.

Dalmaso et al, "Validation of the new Irradiated Nylon™ flocked QUANTISWAB™ for the quantitative recovery of micro-organisms in critical clean room environments", PDA Europe Conference and Exhibition "Best Practices in Aseptic Manufacturing", May 8-9, 2007, Milan, Italy.

Rivers et al, "Evaluation of Expanded Use of Copan Diagnostics' UTM Viral Transport Media and Eswab for the Transportation, Culture, and Nucleic Acid Detection of Trichomonas Vaginalis from Genital Samples", $23_{rd}$ Annual Clinical Virology Symposium—Clearwater Beach, Florida USA, Apr. 29-May 2, 2007.

Castriciano et al, "Self-Collection of Nasal Respiratory Tract Sampling by Volunteers Using the Copan Nasal Flocked Swabs Design", $23^{rd}$ Annual Clinical Virology Symposium—Clearwater Beach, Florida USA, Apr. 29-May 2, 2007.

Castriciano et al, "Sampling Respiratory Epithelial Cells by Nasal or Nasopharyngeal Flocked Swabs", $17^{th}$ European Congress of Clinical Microbiology and Infectious Diseases, Munich, Germany, Mar. 31-Apr. 3, 2007.

Castriciano et al, "Flocked Swabs and UTM-RT are Pre-Analytical Tools Suitable for Rapid Antigen Kits, Direct Immunofluorescence, Culture and PCR Diagnostics Assay for Viral Infections", $17^{th}$ European Congress of Clinical Microbiology and Infectious Diseases, Munich, Germany, Mar. 31-Apr. 3, 2007.

Hjelmevoll et al, "Clinical Validation of a Real-Time Polymerase Chain Reaction Detection of Neisseria gonorrheae porA Pseudogene Versus Culture Techniques", Sexually Transmitted Diseases, May 2008, vol. 35, No. 5, pp. 517-520.

Shokoples et al, "Evaluation of Clearview→RSV and RSV Respi-Strip for the Rapid Detection of RSV from Nasopharyngeal Swabs", $23^{rd}$ Annual Clinical Virology Symposium—Clearwater Beach, Florida USA, Apr. 29-May 2, 2007.

Lindh et al, "Orthomyxo-, paramyxo- and flavivirus infections in wild waterfowl in Finland", Virology Journal 2008, Feb. 28, 2008.

Walsh et al, "Pediatric Respiratory Infectious Disease Analysis: UTM-RT Versus Flocked Swab Nasal Collections", $23^{rd}$ Annual Clinical Virology Symposium—Clearwater Beach, Florida USA, Apr. 29-May 2, 2007.

Starkey et al, "Respiratory Viral Recovery from Pediatric Nasopharyngeal Specimens Using Flocked Swab", Clinical Virology Symposium—CVS 2008, Apr. 27, 2008.

Schenk, "Flock Trials in Laboratory with Alternating Current", 6. Internationales Flockseminar, Sep. 8-10, 1980 pp. 135-150.

Castriciano et al, "Increased Rates of Respiratory Viral [RV] Infections Using Flocked Swabs and UTM-RT", $17^{th}$ European Congress of Clinical Microbiology and Infectious Diseases, Munich, Germany, Mar. 31-Apr. 3, 2007.

Davidson et al, "Evaluation of Flocked Nylon Swabs (Copan Eswab) for Detection of Bacterial Pathogens by Culture and PCR", ASM 2007, American Society for Microbiology, Toronto, Canada—May 21-25, 2007.

U.S. Federal Register, Wednesday, Aug. 14, 2002, 49 CFR 171 et al., Hazardous Materials: Revision to Standards for Infectious Substances, Final Rule.

Declaration of Daniele Triva Under 37 CFR §1.132 dated Jun. 24, 2008, filed in U.S. Appl. No. 10/543,873, bearing USPTO date stamp of Jul. 3, 2008.

Body et al. "Quality Control of Microbiological Transport Systems; Approved Standard", (2003) NCCLS vol. 23, No. 34.

Grafe et al "Polymeric Nanofibers and Nanofiber Webs: A New Class of Nonwovens" to be presented at INTC 2002: International Nonwovens Technical Conference (Joint INDA-TAPPI Conference) Atlanta, GA, Sep. 24-26, 2002.

Ndaro et al. "Splitting of Islands-in-the-Sea Fibers (PA6/COPET) During Hydroentangling of Nonwovens" Journal of Engineered Fibers and Fabrics, vol. 2, Issue 4—2007, pp. 1-9.

US Patent Office, Office Actions/Communications dated Jan. 5, 2012, Dec. 20, 2011, Dec. 1, 2011, Aug. 10, 2011, in U.S. Appl. No. 10/543,873, titled "Swab for Collecting Biological Specimens", Triva.

Submissions by applicants dated Jan. 4, 2012, Dec. 16, 2011, Dec. 12, 2011 and May 27, 2011, in U.S. Appl. No. 10/543,873, titled "Swab for Collecting Biological Specimens".

US Patent Office, Office Actions/Communications dated Dec. 1, 2011 and Oct. 29, 2010, in U.S. Appl. No. 12/903,921, titled "Swab for Collecting Biological Specimens", Triva.

Submissions by applicants dated Mar. 1, 2012 and Oct. 13, 2010 , in U.S. Appl. No. 12/903,921, titled "Swab for Collecting Biological Specimens".

Page 1179 of The American Heritage Dictionary, Second College Edition (1985, Houghton Mifflin Company, Boston, MA).

EP1358818(A1) Gueret (Nov. 5, 2003)—Abstract "Device for applying a product, especially cosmetics, covered with a flocking of different fibre types".

CN2554995(Y), Weng et al (Abstract) published Jun. 11, 2003 "Sampler for uterine cervix".

CN1070850(A) Fuyuan (Abstract) Published Apr. 14, 1993 "constant temp. electrostatic flocking method and equipment".

CN2479505(Y) Wang (Abstract) published Feb. 27, 2002 "Microbial teting box".

DE10246379(A1) Jenner (Abstract) published Apr. 15, 2004 "Flock-coated cosmetic-applicator head has hollow basic body containing applicator holes, flock-coated surface, adhesive applicator by pressurized air".

Office Action dated Oct. 6, 2011, issued in connection with Canadian Patent Application No. 2,744,678.

Anantharamaiah et al, "Durable Nonwoven Fabrics via Fracturing Bicomponent Islands-in-the-Sea Filaments", Journal of Engineered Fibers and Fabrics, vol. 3, Issue 3, pp. 1-9, 2008.

(56) References Cited

OTHER PUBLICATIONS

Ofice Action dated Oct. 12, 2011, issued in connection with Canadian Patent Application No. 2,744,282.
Office Action dated Feb. 3, 2012 relating to Australian Patent Application No. 2010341421 of Puritan Medical Products Company, LLC. Swayam Chintamani, Patent Examination A.
Office Action dated Feb. 3, 2012 relating to Australian Patent Application No. 2010341422 of Puritan Medical Products Company, LLC. Swayam Chintamani, Patent Examination A.
Office Action dated Feb. 13, 2012 relating to Canadian Patent Application No. 2,744,678 of Puritan Medical Products Company, LLC. Patrick Norman, Patent Examiner.
Notice of Allowance dated Feb. 9, 2012 in Canadian Patent Application No. 2,744,282 of Puritan Medical Products Company, LLC.
"Studies on Physical and Microbiological Characteristics of Selected Clinical Swabs" (Dec. 7, 2009) produced by Clean Earth Technologies, LLC, Kunapuli T Madhusudhan, Ph.D., Program Manager, Clean Earth Technoogies, LLC, Winston-Salem, NC 27101.

* cited by examiner

COLLECTION DEVICE AND MATERIAL

The present application is a continuation of application Ser. No. 12/849,343 (U.S. Pat. No. 8,334,134), filed Aug. 3, 2010 (published as US 2011-0262952-A 1), which claims benefit of U.S. Provisional Application No. 61/326,466, filed Apr. 21, 2010, the entire contents of each of which is incorporated herein by reference.

TECHNICAL FIELD

The present disclosure describes a swab, and collection material for use therein, for collecting biological specimens.

BACKGROUND

Devices, such as swabs, for collecting biological specimens of organic material are known in the field of clinical and diagnostic analyses, which generally include a cylindrical rod or stick containing on a collection end or tip a wad of fiber material, such as rayon or a natural fiber such as cotton, with hydrophilic properties to allow rapid absorption of the quantity of specimen to be collected and tested. Stable adherence of the fiber wrapped around the end or tip of the rod or stick is generally achieved by gluing.

Collection swabs containing the collected material are often immersed in a culture media, such as in a test tube, vial, culture dish, or culture bottle, soon or immediately after collection to preserve and conserve the collected specimen during storage and/or transport to, for example, an analytical laboratory. Collection swabs and devices of the prior art are described, for example, in EP0643131 and WO2004/086979.

SUMMARY

Devices, such as swabs, and materials of the present disclosure, and methods of making same, include randomly arranged sea-island bicomponent fibers which have randomly splayed terminal ends.

The present disclosure provides a swab for collecting and releasing a biological sample containing an applicator and sea-island bicomponent fibers, wherein at least about 85% of the fibers comprise randomly splayed terminal ends of the islands of said bicomponent fibers along a length of about 50% or less from the ends.

The swab of present disclosure contain fibers attached to an end portion of the applicator, such as by adhesive.

The present disclosure provides a method of forming the swab of the disclosure which includes adhering the bicomponent fibers to the applicator, removing a portion of the sea component of the bicomponent fibers in a heated alkaline solvent, and forming the randomly splayed fibers by application of mechanical force to the ends of the fibers which have had the sea component removed.

The present disclosure provides a method of collecting a biological sample which includes contacting the swab of the disclosure with a source of biological material such that a sample of the material is retained by the swab.

DETAILED DESCRIPTION

Devices, such as swabs, and materials of the present disclosure, and methods of making same, include randomly arranged sea-island bicomponent fibers which have randomly splayed terminal ends.

Materials of the present disclosure may be included as a high absorbency member of medical swab devices. The "splitable" flock fiber materials of the present disclosure attached to the end of a thin "stick-like" polymeric shaft are described and contemplated herein as swabs of the present disclosure. The flock fibers of the disclosure, which are physico-chemically "split" at the end of the material, provide a fibrous material with fibrous surface area which increase the overall surface area of the fibrous mass. This leads to a higher degree of fluid absorption by the fibrous mass.

The materials of the disclosure may include micro- and nano-fibers, such as bicomponent sea-island materials. Segmented pie materials may also be used. Bicomponent sea-island materials and segmented pie materials are known and described, for example in Ndaro et al Journal of Engineered Fibers and Fabrics, volume 2, Issue 4, 2007 "Splitting of Islands-in-the-Sea Fibers (PA6/COPET) During Hydroentangling of Nonwovens"; and Fedorova, Nataliya "Investigation of the Utility of Islands-in-the-sea Bicomponent Fiber Technology in the SpunBond Process" Ph.D. Dissertation, North Carolina State University, Raleigh, N.C. (2006); as well as in U.S. Patent Application Publication Nos.: 20100075143 (FIBER STRUCTURE AND METHOD FOR PRODUCTION THEREOF), 20100068516 (THERMOPLASTIC FIBER WITH EXCELLENT DURABILITY AND FABRIC COMPRISING THE SAME), and 20100029158 (ISLANDS-IN-SEA TYPE COMPOSITE FIBER AND PROCESS FOR PRODUCING SAME), And WO2002042528 (A SEA-ISLAND TYPED COMPOSITE FIBER USED IN WARP KNITTING, AND A PROCESS OF PREPARING FOR THE SAME), WO2002042529 A SEA-ISLAND TYPE COMPOSITE FIBER FOR RAISED WARP KNIT FABRIC, AND A PROCESS OF PREPARING FOR THE SAME), WO2002088438 (A SEA-ISLAND TYPED CONJUGATE MULTI FILAMENT COMPRISING DOPE DYEING COMPONENT, AND A PROCESS OF PREPARING FOR THE SAME), and as are commercially available from, for example, Kolon Industry, Kumi City, Kyungbuk, Korea and generally described as ROJEL—polyester/polyester conjugated fiber yarn (sea/island) or SPECIAL TYPE OF ROJEL—polyester/nylon conjugated fiber yarn (sea/island); or Hyosung Corporation, Ulsan City, Kyungbuk, Korea and generally described as MIPAN XF—Nylon/polyester conjugated yarn (pie-wedge cross-section).

In the islands-in-sea type composite fiber of the presently described material, an easily soluble polymer is incorporated for the sea portion and preferably contains at least one polymer easily soluble in aqueous alkali solutions, such as polylactic acid, super high molecular weight polyalkyleneoxide-condensate polymers, polyethyleneglycol compound-copolymerized polyesters, and copolymerized polyesters of polyethylene glycol (PAG) compounds with 5-sodium sulfoisophthalic acid or dimethyl-5-sulfoisophthalate sodium salt (DMIS). Polyester sea materials may include alkali soluble copolymer polyester materials with polyester mainly containing polyethylene terephthalate of more than 90 mole percent as island component (such as is described, for example, in WO2002042528, the entire contents of which is incorporated herein by reference).

The islands-in-sea type bicomponent composite fiber of the present disclosure contains a sea part containing or composed of polymer of greater solubility than a plurality of island parts containing or composed of a less soluble polymer, in the cross-sectional profile of which the number of the island parts is about 10, 24, 36, 37, 64 or 240 islands per fiber, or ranges of islands per fiber between any of 10, 24, 36, 37, 64, 240 or 3000 islands per fiber.

The island component of the bicomponent composite fiber of the present disclosure may be a polyamide, such as nylon, or a polyester. Examples of the polyamide include polymers having an amide bond, such as nylon 6, nylon 66, nylon 610, and nylon 12. The polyester is not particularly limited as long as it is a polymer synthesized from dicarboxylic acid or an ester-forming derivative and diol or an ester-forming derivative thereof and can be used as the fiber. Specific examples thereof include polyethylene terephthalate, polytrimethylene terephthalate, polytetramethylene terephthalate, polycyclohexylenedimethylene terephthalate, polyethylene-2,6-naphthalene dicarboxylate, polyethylene-1,2-bis(2-chlorophenoxy)ethane-4,4'-dicarboxylate and the like. In an embodiment of the present invention, a polyethylene terephthalate or a polyester copolymer containing mainly an ethylene terephthalate unit, may be used.

The islands-in-sea type bicomponent composite fiber of the present disclosure have a linear mass density in the range of about 1-7 deniers, alternatively in the range of about 2 to 6 deniers or the range of 2 to 5.8 deniers (or 2.22 to 6.49 dtex) wherein a denier is the mass in grams per 9000 meters of fiber and dtex is the mass in grams per 10,000 meters. The diameter (ø, in centimeters) of a bicomponent composite fiber may be estimated from the following formula, wherein ρ represents a materials density in grams per cubic centimeter:

$$\varnothing = \sqrt{\frac{4 \times 10^{-6} \cdot dtex}{\pi \rho}}$$

Estimating the fiber specific gravity as being equal to 1 (specific gravity values of common fiber polymers according to Gafe et al ("Polymeric Nanofibers and Nanofiber Webs: A New Class of Nonwovens" INTC 2002: International Nonwovens Technical Conference (Joint INDA—TAPPI Conference), Atlanta, Ga., Sep. 24-26, 2002) are as follows: 0.92 (polypropylene or PP), 1.14 (polyamide 66 or nylon or PA66) and 1.38 (polyethylene terephthalate or PET)), the diameter of bicomponent composite fiber of the present disclosure having a linear mass density in the range of 2 to 5.8 deniers would be about 16.7 µm to 28.6 µm.

The islands of the bicomponent composite fibers of the present disclosure have a mass linear density of about 0.01 to about 0.3 deniers, or about 0.05 to about 0.2 deniers, or about 0.06 to about 0.16 deniers, depending on the linear mass density of the bicomponent composite fibers of the present disclosure.

The islands-in-sea type bicomponent composite fibers of the material of the present disclosure have a length, or cut length, of about 10 to about 100 thousandths of an inch (about 254 µm to about 2,540 µm), or about 20 to about 90 thousandths of an inch, or about 20 to about 80 thousandths of an inch, or about 20 to about 70 thousandths of an inch, or about 20 to about 60 thousandths of an inch.

At least about 50%, 55%, 60%, 70%, 75%, 80%, 85%, 90% or 95% (by number) of the islands-in-sea type bicomponent composite fibers of the material of the present disclosure contain randomly splayed, or split and spread, terminal ends along a length of about 50%, 45%, 40%, 35%, 30%, 25%, 20%, 15% or 10% or less from one end.

At least about 50%, (by number) of the islands-in-sea type bicomponent composite fibers of the material of the present disclosure contain randomly splayed, or split and spread, terminal ends along a length of about 50% or less from one end.

At least about 50%, (by number) of the islands-in-sea type bicomponent composite fibers of the material of the present disclosure contain randomly splayed, or split and spread, terminal ends along a length of about 45% or less from one end.

At least about 50%, (by number) of the islands-in-sea type bicomponent composite fibers of the material of the present disclosure contain randomly splayed, or split and spread, terminal ends along a length of about 40% or less from one end.

At least about 50%, (by number) of the islands-in-sea type bicomponent composite fibers of the material of the present disclosure contain randomly splayed, or split and spread, terminal ends along a length of about 35% or less from one end.

At least about 50%, (by number) of the islands-in-sea type bicomponent composite fibers of the material of the present disclosure contain randomly splayed, or split and spread, terminal ends along a length of about 30% or less from one end.

At least about 50%, (by number) of the islands-in-sea type bicomponent composite fibers of the material of the present disclosure contain randomly splayed, or split and spread, terminal ends along a length of about 25% or less from one end.

At least about 50%, (by number) of the islands-in-sea type bicomponent composite fibers of the material of the present disclosure contain randomly splayed, or split and spread, terminal ends along a length of about 20% or less from one end.

At least about 50%, (by number) of the islands-in-sea type bicomponent composite fibers of the material of the present disclosure contain randomly splayed, or split and spread, terminal ends along a length of about 15% or less from one end.

At least about 50%, (by number) of, the islands-in-sea type bicomponent composite fibers of the material of the present disclosure contain randomly splayed, or split and spread, terminal ends along a length of about 10% or less from one end.

At least about 55%, (by number) of the islands-in-sea type bicomponent composite fibers of the material of the present disclosure contain randomly splayed, or split and spread, terminal ends along a length of about 50% or less from one end.

At least about 55%, (by number) of the islands-in-sea type bicomponent composite fibers of the material of the present disclosure contain randomly splayed, or split and spread, terminal ends along a length of about 45% or less from one end.

At least about 55%, (by number) of the islands-in-sea type bicomponent composite fibers of the material of the present disclosure contain randomly splayed, or split and spread, terminal ends along a length of about 40% or less from one end.

At least about 55%, (by number) of the islands-in-sea type bicomponent composite fibers of the material of the present disclosure contain randomly splayed, or split and spread, terminal ends along a length of about 35% or less from one end.

At least about 55%, (by number) of the islands-in-sea type bicomponent composite fibers of the material of the present disclosure contain randomly splayed, or split and spread, terminal ends along a length of about 30% or less from one end.

At least about 55%, (by number) of the islands-in-sea type bicomponent composite fibers of the material of the present disclosure contain randomly splayed, or split and spread, terminal ends along a length of about 25% or less from one end.

At least about 55%, (by number) of the islands-in-sea type bicomponent composite fibers of the material of the present disclosure contain randomly splayed, or split and spread, terminal ends along a length of about 20% or less from one end.

At least about 55%, (by number) of the islands-in-sea type bicomponent composite fibers of the material of the present disclosure contain randomly splayed, or split and spread, terminal ends along a length of about 15% or less from one end.

At least about 55%, (by number) of the islands-in-sea type bicomponent composite fibers of the material of the present disclosure contain randomly splayed, or split and spread, terminal ends along a length of about 10% or less from one end.

At least about 60%, (by number) of the islands-in-sea type bicomponent composite fibers of the material of the present disclosure contain randomly splayed, or split and spread, terminal ends along a length of about 50% or less from one end.

At least about 60%, (by number) of the islands-in-sea type bicomponent composite fibers of the material of the present disclosure contain randomly splayed, or split and spread, terminal ends along a length of about 45% or less from one end.

At least about 60%, (by number) of the islands-in-sea type bicomponent composite fibers of the material of the present disclosure contain randomly splayed, or split and spread, terminal ends along a length of about 40% or less from one end.

At least about 60%, (by number) of the islands-in-sea type bicomponent composite fibers of the material of the present disclosure contain randomly splayed, or split and spread, terminal ends along a length of about 35% or less from one end.

At least about 60%, (by number) of the islands-in-sea type bicomponent composite fibers of the material of the present disclosure contain randomly splayed, or split and spread, terminal ends along a length of about 30% or less from one end.

At least about 60%, (by number) of the islands-in-sea type bicomponent composite fibers of the material of the present disclosure contain randomly splayed, or split and spread, terminal ends along a length of about 25% or less from one end.

At least about 60%, (by number) of the islands-in-sea type bicomponent composite fibers of the material of the present disclosure contain randomly splayed, or split and spread, terminal ends along a length of about 20% or less from one end.

At least about 60%, (by number) of the islands-in-sea type bicomponent composite fibers of the material of the present disclosure contain randomly splayed, or split and spread, terminal ends along a length of about 15% or less from one end.

At least about 60%, (by number) of the islands-in-sea type bicomponent composite fibers of the material of the present disclosure contain randomly splayed, or split and spread, terminal ends along a length of about 10% or less from one end.

At least about 70%, (by number) of the islands-in-sea type bicomponent composite fibers of the material of the present disclosure contain randomly splayed, or split and spread, terminal ends along a length of about 50% or less from one end.

At least about 70%, (by number) of the islands-in-sea type bicomponent composite fibers of the material of the present disclosure contain randomly splayed, or split and spread, terminal ends along a length of about 45% or less from one end.

At least about 70%, (by number) of the islands-in-sea type bicomponent composite fibers of the material of the present disclosure contain randomly splayed, or split and spread, terminal ends along a length of about 40% or less from one end.

At least about 70%, (by number) of the islands-in-sea type bicomponent composite fibers of the material of the present disclosure contain randomly splayed, or split and spread, terminal ends along a length of about 35% or less from one end.

At least about 70%, (by number) of the islands-in-sea type bicomponent composite fibers of the material of the present disclosure contain randomly splayed, or split and spread, terminal ends along a length of about 30% or less from one end.

At least about 70%, (by number) of the islands-in-sea type bicomponent composite fibers of the material of the present disclosure contain randomly splayed, or split and spread, terminal ends along a length of about 25% or less from one end.

At least about 70%, (by number) of the islands-in-sea type bicomponent composite fibers of the material of the present disclosure contain randomly splayed, or split and spread, terminal ends along a length of about 20% or less from one end.

At least about 70%, (by number) of the islands-in-sea type bicomponent composite fibers of the material of the present disclosure contain randomly splayed, or split and spread, terminal ends along a length of about 15% or less from one end.

At least about 70%, (by number) of the islands-in-sea type bicomponent composite fibers of the material of the present disclosure contain randomly splayed, or split and spread, terminal ends along a length of about 10% or less from one end.

At least about 75%, (by number) of the islands-in-sea type bicomponent composite fibers of the material of the present disclosure contain randomly splayed, or split and spread, terminal ends along a length of about 50% or less from one end.

At least about 75%, (by number) of the islands-in-sea type bicomponent composite fibers of the material of the present disclosure contain randomly splayed, or split and spread, terminal ends along a length of about 45% or less from one end.

At least about 75%, (by number) of the islands-in-sea type bicomponent composite fibers of the material of the present disclosure contain randomly splayed, or split and spread, terminal ends along a length of about 40% or less from one end.

At least about 75%, (by number) of the islands-in-sea type bicomponent composite fibers of the material of the present disclosure contain randomly splayed, or split and spread, terminal ends along a length of about 35% or less from one end.

At least about 75%, (by number) of the islands-in-sea type bicomponent composite fibers of the material of the present disclosure contain randomly splayed, or split and spread, terminal ends along a length of about 30% or less from one end.

At least about 75%, (by number) of the islands-in-sea type bicomponent composite fibers of the material of the present disclosure contain randomly splayed, or split and spread, terminal ends along a length of about 25% or less from one end.

At least about 75%, (by number) of the islands-in-sea type bicomponent composite fibers of the material of the present disclosure contain randomly splayed, or split and spread, terminal ends along a length of about 20% or less from one end.

At least about 75%, (by number) of the islands-in-sea type bicomponent composite fibers of the material of the present disclosure contain randomly splayed, or split and spread, terminal ends along a length of about 15% or less from one end.

At least about 75%, (by number) of the islands-in-sea type bicomponent composite fibers of the material of the present disclosure contain randomly splayed, or split and spread, terminal ends along a length of about 10% or less from one end.

At least about 80%, (by number) of the islands-in-sea type bicomponent composite fibers of the material of the present disclosure contain randomly splayed, or split and spread, terminal ends along a length of about 50% or less from one end.

At least about 80%, (by number) of the islands-in-sea type bicomponent composite fibers of the material of the present disclosure contain randomly splayed, or split and spread, terminal ends along a length of about 45% or less from one end.

At least about 80%, (by number) of the islands-in-sea type bicomponent composite fibers of the material of the present disclosure contain randomly splayed, or split and spread, terminal ends along a length of about 40% or less from one end.

At least about 80%, (by number) of the islands-in-sea type bicomponent composite fibers of the material of the present disclosure contain randomly splayed, or split and spread, terminal ends along a length of about 35% or less from one end.

At least about 80%, (by number) of the islands-in-sea type bicomponent composite fibers of the material of the present disclosure contain randomly splayed, or split and spread, terminal ends along a length of about 30% or less from one end.

At least about 80%, (by number) of the islands-in-sea type bicomponent composite fibers of the material of the present disclosure contain randomly splayed, or split and spread, terminal ends along a length of about 25% or less from one end.

At least about 80%, (by number) of the islands-in-sea type bicomponent composite fibers of the material of the present disclosure contain randomly splayed, or split and spread, terminal ends along a length of about 20% or less from one end.

At least about 80%, (by number) of the islands-in-sea type bicomponent composite fibers of the material of the present disclosure contain randomly splayed, or split and spread, terminal ends along a length of about 15% or less from one end.

At least about 80%, (by number) of the islands-in-sea type bicomponent composite fibers of the material of the present disclosure contain randomly splayed, or split and spread, terminal ends along a length of about 10% or less from one end.

At least about 85%, (by number) of the islands-in-sea type bicomponent composite fibers of the material of the present disclosure contain randomly splayed, or split and spread, terminal ends along a length of about 50% or less from one end.

At least about 85%, (by number) of the islands-in-sea type bicomponent composite fibers of the material of the present disclosure contain randomly splayed, or split and spread, terminal ends along a length of about 45% or less from one end.

At least about 85%, (by number) of the islands-in-sea type bicomponent composite fibers of the material of the present disclosure contain randomly splayed, or split and spread, terminal ends along a length of about 40% or less from one end.

At least about 85%, (by number) of the islands-in-sea type bicomponent composite fibers of the material of the present disclosure contain randomly splayed, or split and spread, terminal ends along a length of about 35% or less from one end.

At least about 85%, (by number) of the islands-in-sea type bicomponent composite fibers of the material of the present disclosure contain randomly splayed, or split and spread, terminal ends along a length of about 30% or less from one end.

At least about 85%, (by number) of the islands-in-sea type bicomponent composite fibers of the material of the present disclosure contain randomly splayed, or split and spread, terminal ends along a length of about 25% or less from one end.

At least about 85%, (by number) of the islands-in-sea type bicomponent composite fibers of the material of the present disclosure contain randomly splayed, or split and spread, terminal ends along a length of about 20% or less from one end.

At least about 85%, (by number) of the islands-in-sea type bicomponent composite fibers of the material of the present disclosure contain randomly splayed, or split and spread, terminal ends along a length of about 15% or less from one end.

At least about 85%, (by number) of the islands-in-sea type bicomponent composite fibers of the material of the present disclosure contain randomly splayed, or split and spread, terminal ends along a length of about 10% or less from one end.

At least about 90%, (by number) of the islands-in-sea type bicomponent composite fibers of the material of the present disclosure contain randomly splayed, or split and spread, terminal ends along a length of about 50% or less from one end.

At least about 90%, (by number) of the islands-in-sea type bicomponent composite fibers of the material of the present disclosure contain randomly splayed, or split and spread, terminal ends along a length of about 45% or less from one end.

At least about 90%, (by number) of the islands-in-sea type bicomponent composite fibers of the material of the present disclosure contain randomly splayed, or split and spread, terminal ends along a length of about 40% or less from one end.

At least about 90%, (by number) of the islands-in-sea type bicomponent composite fibers of the material of the present disclosure contain randomly splayed, or split and spread, terminal ends along a length of about 35% or less from one end.

At least about 90%, (by number) of the islands-in-sea type bicomponent composite fibers of the material of the present disclosure contain randomly splayed, or split and spread, terminal ends along a length of about 30% or less from one end.

At least about 90%, (by number) of the islands-in-sea type bicomponent composite fibers of the material of the present disclosure contain randomly splayed, or split and spread, terminal ends along a length of about 25% or less from one end.

At least about 90%, (by number) of the islands-in-sea type bicomponent composite fibers of the material of the present disclosure contain randomly splayed, or split and spread, terminal ends along a length of about 20% or less from one end.

At least about 90%, (by number) of the islands-in-sea type bicomponent composite fibers of the material of the present disclosure contain randomly splayed, or split and spread, terminal ends along a length of about 15% or less from one end.

At least about 90%, (by number) of the islands-in-sea type bicomponent composite fibers of the material of the present disclosure contain randomly splayed, or split and spread, terminal ends along a length of about 10% or less from one end.

At least about 95%, (by number) of the islands-in-sea type bicomponent composite fibers of the material of the present disclosure contain randomly splayed, or split and spread, terminal ends along a length of about 50% or less from one end.

At least about 95%, (by number) of the islands-in-sea type bicomponent composite fibers of the material of the present disclosure contain randomly splayed, or split and spread, terminal ends along a length of about 45% or less from one end.

At least about 95%, (by number) of the islands-in-sea type bicomponent composite fibers of the material of the present disclosure contain randomly splayed, or split and spread, terminal ends along a length of about 40% or less from one end.

At least about 95%, (by number) of the islands-in-sea type bicomponent composite fibers of the material of the present disclosure contain randomly splayed, or split and spread, terminal ends along a length of about 35% or less from one end.

At least about 95%, (by number) of the islands-in-sea type bicomponent composite fibers of the material of the present disclosure contain randomly splayed, or split and spread, terminal ends along a length of about 30% or less from one end.

At least about 95%, (by number) of the islands-in-sea type bicomponent composite fibers of the material of the present disclosure contain randomly splayed, or split and spread, terminal ends along a length of about 25% or less from one end.

At least about 95%, (by number) of the islands-in-sea type bicomponent composite fibers of the material of the present disclosure contain randomly splayed, or split and spread, terminal ends along a length of about 20% or less from one end.

At least about 95%, (by number) of the islands-in-sea type bicomponent composite fibers of the material of the present disclosure contain randomly splayed, or split and spread, terminal ends along a length of about 15% or less from one end.

At least about 95%, (by number) of the islands-in-sea type bicomponent composite fibers of the material of the present disclosure contain randomly splayed, or split and spread, terminal ends along a length of about 10% or less from one end.

Figure 1:
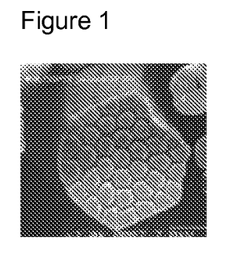
FIG. 1 provides an end view of a bicomponent fiber of PET/PET.
Figure 2:
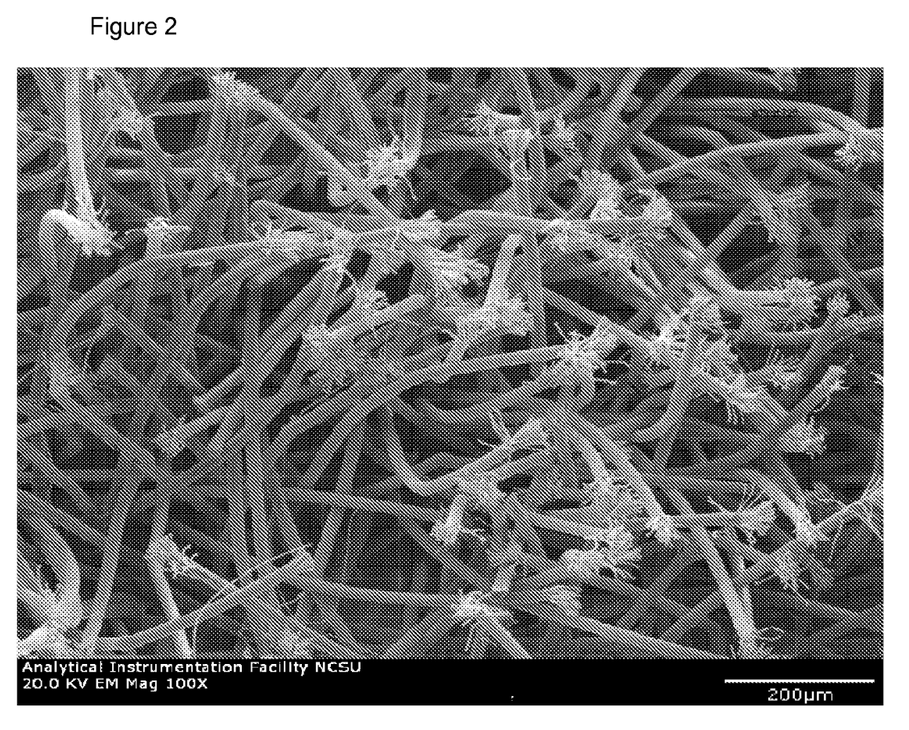
FIG. 2 is an electron micrograph of randomly arranged sea-island bicomponent PET/PET fibers which have randomly splayed terminal ends.

FIG. 2 is a scanning photograph of an example of material of the present disclosure wherein randomly splayed ends of the bicomponent composite fibers is illustrated.

The material of the present disclosure alternatively contains islands-in-sea type bicomponent composite fibers wherein at least about 85% to about 95% (by number) of the bicomponent composite fibers contain randomly splayed terminal ends along a length of about 40% or less from one end. The material of the present disclosure alternatively contains islands-in-sea type bicomponent composite fibers wherein at least about 85% to about 95% (by number) of the bicomponent composite fibers contain randomly splayed terminal ends along a length of about 30% or less from one end.

One average, a material of the present disclosure may contain islands-in-sea type bicomponent composite fibers wherein about 100% (by number) of the bicomponent composite fibers contain randomly splayed terminal ends along a length of about 20% or less from one end.

The exemplary method of the present disclosure has produced a distribution of fibers containing randomly splayed terminal ends along a length of about 0% to about 10% from the end of the fiber in about 50% (by number) of the fibers, fibers containing randomly splayed terminal ends along a length of about 10% to about 20% from the end of the fiber in about 40% (by number) of the fibers, and fibers containing randomly splayed terminal ends along a length of about 20% to about 100% from the end of the fiber in about 10% (by number) of the fibers.

The bicomponent composite fibers of the material of the present disclosure are preferably randomly arranged.

The percent by number of fibers of the present disclosure containing randomly splayed terminal ends may be evaluated by light microscope (Amscope) at 180× power with a 1 mm calibration scale (NIST) in conjunction with a video camera (Amscope 3.0 megapixel) and suitable video analysis software, such as for example, Version 3.0.12.498 Amscope video software calibrated to 180×.

A swab of the present disclosure, which includes material of the present disclosure, may be any shape adapted for collection, and optional retention, of biological samples from a host directly or already collected biological fluid or sample. Shapes and sizes of such devices are known in the art. The swab of the present disclosure is constructed of materials known in the art, such as acrylonitrile-butadiene-styrene (ABS). The swab of the present disclosure is such that the material of the present disclosure may be attached to the applicator of the swab through an adhesive during a flocking technique known in the art.

An applicator of the swab of the present disclosure may be a rod or rod-like thermoplastic substrate wherein one end is coated, partially, substantially or completely, with an adhesive to anchor or hold fibers of the present disclosure to the substrate in an initial arrangement generally perpendicular to the substrate and generally parallel to adjacent fibers to thereby create, for example, a bristle or bristly end on the substrate.

In a method of making devices according to the present disclosure, individual, loose or connected substrate, such as applicator shafts, sticks or rods have adhesive applied by at least one adhesive applicator container, block, head, nozzle, or roller by, for example, spraying, dipping, rolling, printing or a combination thereof, optionally in a metered fashion, under pressure or by gravity, and in a manner which may or may not include any combination of linear and/or rotational, such as by axial rotation or spinning, of the adhesive applicator relative to the applicator.

In the flocking technique of the present disclosure, an electric field of alternating or direct current is applied to the fibers in a manner know in the art to organize and transport charged fibers to opposite charged adhesive-covered substrate such that the fibers are held in place by the tackiness or adhesive strength of the adhesive, only in areas where the adhesive has been applied to produce flock fiber tipped applicators, or swabs of the disclosure. The technique may include movement of the substrate, linearly and/or rotationally, such as by axial rotation or spinning, at any time or throughout the process of applying fibers to the adhesive. Where further curing of the adhesive, such as by light or heat, is required, the flock fiber tipped applicator swab may be treated with light and/or heat so as to cure the adhesive.

Swabs of the disclosure may contain approximately $10^4$ to approximately $10^{10}$, or approximately $10^4$ to approximately $10^9$, or approximately $10^4$ to approximately $10^8$, or approximately $10^4$ to approximately $10^7$, or approximately $10^4$ to approximately $10^6$, or approximately $10^4$ to approximately $10^5$, flock fibers per substrate.

Once applied and secured to the substrate of the disclosure by flocking, the sea component of the bicomponent fibers adhered to the substrate or applicator is partially extracted to the extent described herein, such as by microwave radiation and sonication, to provide islands of the fibers which are subsequently forced in to a random splayed formation, as described herein by application of, for example, mechanical force, such as by blotting. Alternatively, the sea component may be partially extracted to the extent described herein to provide randomly arrange islands of the fibers by, for example, contacting, applying or admixing with a heated alkali solvent or solution, which are subsequently forced in to a random splayed formation, as described herein by application of, for example, mechanical force, such as by blotting. A process of the disclosure thereby forces substantially perpendicular flocked fibers at the tip or end of the substrate or applicator device to a random arrangement with randomly splayed or open islands of the original bicomponent fiber. The resulting randomly splayed arrangement of the island fibers are alternatively described as being in a flower arrangement as a flower flock.

The material of the disclosure may be made in a similar manner without requiring securing of the material to the substrate wherein the sea component is partially extracted and subsequent application of, for example, microwave radiation and sonication, or partial extraction with heat and alkali, and subsequent application of mechanical force, to produce the randomly splayed fiber arrangement described herein.

Application of heat and alkali solutions or solvents are described herein as a means of extracting the sea component of the bicomponent fiber. The choice of extraction protocol is dependent of the relative solubility and properties of the sea and island components such that other extraction protocols are contemplated based on the bicomponent fiber materials described herein and as are generally available.

The adhesive of the present disclosure is not particularly limited and general and photo or heat cured acrylic-based, polyurethane-based, polyamide-based, polyester-based, vinyl-based and/or two-part epoxy adhesives may be used. Silicones, cyanoacrylates, polyurethanes and/or latex adhesives may be used. Polyurethane adhesive are generally known and available, such as from K&W Adhesive Products.

The swabs of the present disclosure are adapted or designed for collection of, for example, biological samples from oral, nasal, ocular, rectal, urethral, or vaginal orifices of a mammal, such as a human, or patient.

The swabs may be used and is designed for collection of a biological specimen by contact with the fibers of the device such that the device may collect, for example, about 35 to about 200 µl, such as 40, 50, 60, 70, 80, 90, 100, 120, 130, 140, 150, 160, 170, 180 or 190 µl, without causing damage or substantial discomfort to the patient during specimen collection.

The swabs of the present disclosure is useful for and in a method of collecting biological specimens. A swab of the present disclosure is of the type containing a rod terminating with a tip covered in the fibers described herein to allow absorption of said specimens, wherein the fibers cover or substantially cover the tip in the form of a layer applied by means of flocking.

The present disclosure further provides a method of collecting a biological sample which includes contacting a swab as described herein with a source of biological material such that a sample of the material is retained by the swab.

The swabs of the disclosure may be provided, for example, as a component part of a collection, transport, culture and/or transport kit or device wherein additional specimen handling containers and/or devices are included and the swab of the present disclosure is specially adapted to be integrated with such other container and/or devices to assure, for example, specimen retention, integrity and/or sterility.

The present disclosure provides a swab for collecting and releasing a biological sample containing sea-island bicomponent fibers, wherein at least about 85% of the fibers contain randomly splayed terminal ends of the islands of said bicomponent fibers along a length of about 50% or less from said ends. The swabs may further contain bicomponent fibers which are composed of a first polyester sea material and a second polyester island material; the first polyester may have a lower melting point than the second polyester and/or the first polyester may have a greater solubility in alkaline solution than the second polyester. The alkaline solution may more specifically be a sodium hydroxide solution—the sodium hydroxide solution may contain about 5% to about 50% by weight sodium hydroxide in water, or alternatively about 10% by weight sodium hydroxide in water. The alkaline solution wherein the first polyester sea material is more soluble than the second polyester sea material may be a heated alkaline solution—the heated alkaline solution alternatively having a temperature of about 170° F. to about 190° F., such as about 180° F.

The present disclosure provides a swab, wherein material described herein is attached to an end portion of an applicator stick or rod. The material may be adhered to the end of the applicator with an adhesive, and the adhesive may be a photocurable acrylic adhesive or a polyurethane adhesive.

The bicomponent fibers of the present disclosure may be composed of a polyethylene terephthalate sea material and a polyamide island material.

The bicomponent fibers of the present disclosure may be composed of or contain 10-3000 island parts per fiber, 10-240 island parts per fiber, 10-64 island parts per fiber, 10-37 island parts per fiber, 10-36 island parts per fiber, 10-24 island parts per fiber, and/or 24-36 island parts per fiber.

The present disclosure provides the fibrous material of the swab described herein. The fibrous material may be incorporated separately as a part of a device other than a swab, such as a filter or cleaning pad or brush.

The present disclosure provides a method of forming a swab of the disclosure involving adhering the bicomponent fibers to an applicator, removing a portion of the sea component of the bicomponent fibers in an alkaline solvent or solution, and forming the randomly splayed fibers by mechanically separating the fibers, such as by blotting, which have had the sea component removed.

A similar method is provided herein for formation of the material of the disclosure involving removing a portion of the sea component of the bicomponent fibers by microwaving and sonicating, or ultrasonic disruption of, said fibers.

The present disclosure provide a method of forming a swab of the disclosure involving adhering the bicomponent fibers to an applicator rod or stick, removing a portion of the sea component of the bicomponent fibers in a heated alkaline solvent or solution, and forming the randomly splayed fibers by mechanical action of mashing or blotting or force applied to the ends of the fibers which have had the sea component removed.

A similar method is provided herein for formation of the material of the disclosure involving removing a portion of the sea component of the bicomponent fibers in a heated alkaline solvent or solution, and forming the randomly splayed fibers by mechanical action of mashing or blotting or force applied to the ends of the fibers which have had the sea component removed.

The following examples further illustrate the materials and methods of the disclosure without limiting same.

EXAMPLE 1

Swabs

A quantity of (about 30 or so) experimental medical swabs were prepared from ABS plastic "sticks" of Puritan Medical Products (Guilford, Me.) with 0.5 mm long (0.020", nominal length, as determined by a Flock-In-Spect flock fiber length optical measurement instrument) Nylon/PET sea/island type flock fiber. Two adhesive systems were employed in these experimental fabrications; the polyurethane rubber (K&W polyurethane adhesive—MECFLOCK L876/1, MEDCO-DUR H5530 two part polyurethane adhesive, mixed 85 grams L876/1 resin and 15 grams H5530 hardener—product of Kissel and Wolf; cured 3 hours at 110° C. or else cured 16 hours at 80° C.) and a UV photo-curable adhesive from Puritan Medical Products.

The following materials and instruments were used in fabrication: ABS (plastic) swab sticks (supplied by Puritan); Maag Flockmaschinen Motion (flock activity) Tester SPG 1000; K & W adhesive in a shallow aluminum dish (adhesive depth about 1 cm); photo-curable adhesive in light-blocked packet; flock screen sifter; and a supply of Nylon/PET 0.5 mm long Flock fibers The experimental swabs were fabricated as follows. The flock activity tester's 4" diameter aluminum base plate is covered (by sifting) with about 2 grams of loose flock. This sample of loose flock was mounted on to the bottom electrode pedestal of the Flock Activity Tester. The end of the swab sticks were perpendicularly dipped into the fluid K & W adhesive to a depth of about 1 cm and slowly removed to produce end-coated swab-sticks. Some swab samples were made using photo-curable adhesive. Water-based acrylic (F1059B Lubrizol Corp.) flock adhesive and other water based adhesives could be used but in some applications may not be as advantageous in splitting methods under investigation. A 3.5 KV/cm strength was applied to the DC electrodes of the Flock Activity Tester (upflocking machine). This causes the flock fibers to align themselves and actively move to the top electrode. As this flock is being propelled from the bottom to the top electrode, the adhesive coated tip plastic swab-stick is then placed in the "flock fiber cloud" about 1 cm from the bottom electrode (source of the activated flock fibers). While in the "flock fiber cloud", the swab-stick was slowly rotated by rolling the stick held in gripping fingers.

Flock fibers fully adhered to the saturate at the (adhesive wet) end of the swab-stick after about a 2 to 5 second flock field immersion time. The swab adhesive was subsequently cured.

Figure 3:
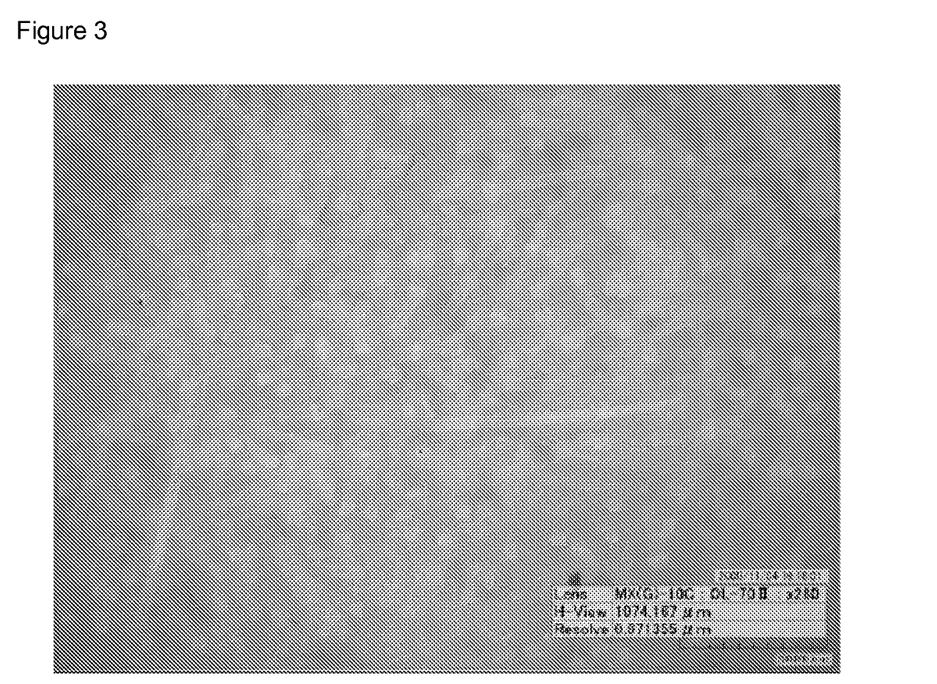
FIG. 3 is a photograph of an experimental swab with an unsplit swab stick head.
Figure 4:
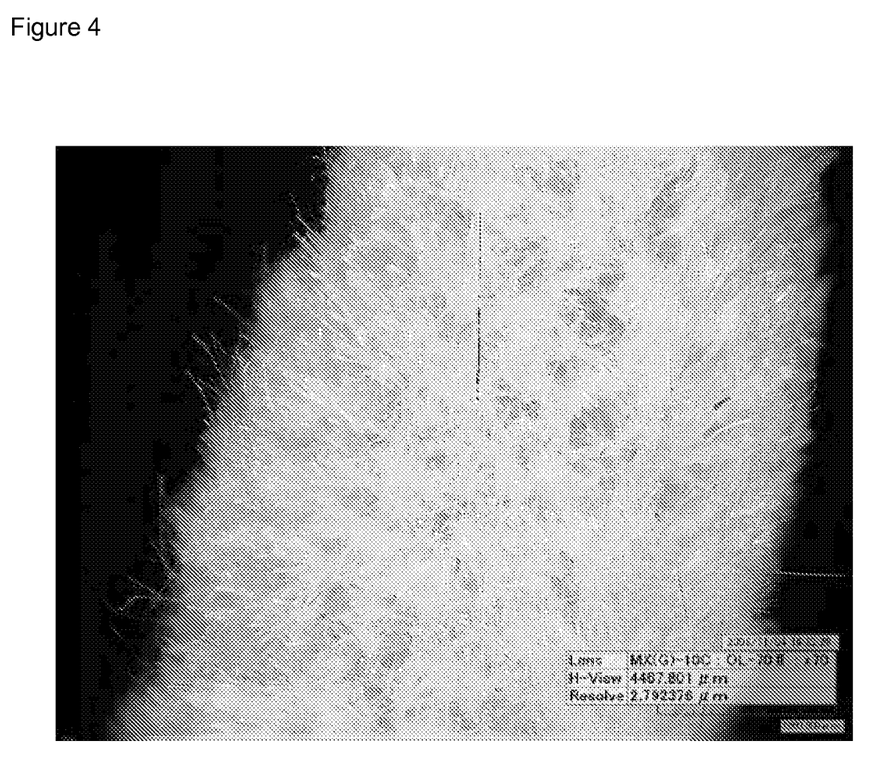
FIG. 4 is a photograph of an experimental swab with a full split swab stick head.

Splitting studies were performed on the swab stick samples in the following manner. In this procedure, the flocked end of the swab-stick was placed into a 400 ml glass beaker containing 50 mls of 5% NaOH solution (enough NaOH solution to cover the flocked end of the swab-stick). The beaker and swab assembly was then placed in the Microwave Oven for 1 minute at high power. The beaker and swab was then Sonicated for 1 minute (5 seconds on—5 seconds off) at 60 power. The flocked swab-sticks were then thoroughly rinsed in tap water. Photographs of the swabs unsplit and split swab-stick heads are show in FIGS. 3 and 4. As an alternative to the use of a microwave and sonication, heated alkaline solution may be used. Mechanical force is used at the ends of the fibers to produce the randomly splayed ends.

The average amount of adhesive and the average amount of flock applied to the ABS base (sticks) were determined by weight with the following results: average weight of "Bare" ABS sticks: 0.5644+/−0.00426 grams; average weight of K & W Adhesive on "Sticks" before flocking: 0.0046 grams; and average weight of PET/Nylon Flock on "Sticks": 0.0135 grams. With an average of 0.0135 grams of sea/island flock fiber on each "stick" this translates to approximately $1.2 \times 10^5$ flock fibers per "stick".

The water "pick-up" capabilities of the flocked medical swabs was determined by a procedure whereby a number of swab and "stick" materials were first weighed (dry). Then this same series of flocked swabs and "sticks" were immersed in room temperature (23° C.) water (tips only) for 5 seconds and then reweighed.

The percent water pick-ups of the various swab configurations were then compared and are presented in Table 1. The results in Table 1 demonstrate that the "bare" ABS swab sticks pick-up or capture little or no water. The polyurethane adhesive coated (tip only) swabs picked up or captures a little water indicating that the adhesive is a more wettable surface that the "bare" ABS. The flocked fiber swab picked up or captured a measurable amount of water (8.95%) while the flocked and split fiber experimental swab picked up or captured the most water (9.25%). The flocked and split fiber swab sample will be expected to pick up or capture more water as compared with the un-split flocked swab if longer (1.0 mm) flock were used.

TABLE 1

| Specimen Description * | Number of Replicates Tested | Average Weight -DRY- (grams) | Average Weight After Tip Water Dip (grams) | Average Water Pick-Up (grams) | Water Pick-Up (based on "dry" stick) |
|---|---|---|---|---|---|
| "Bare" Swab Sticks | 12 | 0.5661 +/− 0.0052 | 0.5665 +/− 0.0049 | 0.0004 | 0.07% (negligible) |
| Swab "Sticks" End Coated with Adhesive | 13 | 0.5790 +/− 0.0050 | 0.5802 +/− 0.0049 | 0.0012 | 0.21% |
| Experimental Swab (Not Split) | 13 | 0.5888 +/− 0.0062 | 0.6415 +/− 0.0084 | 0.0527 | 8.95% |
| Experimental Swabs (Split) | 12 | 0.5913 +/− 0.0047 | 0.6460 +/− 0.0077 | 0.0547 | 9.25% |

Several fiber material types (of sea/island fiber) have been evaluated. The nylon/PET (Kolon) and PET/PET (Kolon-Rojel) fibers appear useful in the fiber flocked medical swab application of the present disclosure. While 0.5 mm long nylon/PET flock fiber were initially investigated, fibers of various sizes may be used and are contemplated.

A sea/island fiber splitting procedure has been developed involving the microwave oven processing of the flock fiber in a 5% NaOH solution followed by a sonication (ultrasonic disruption) treatment.

Two flock adhesives have been found to hold up to the chemical fiber splitting procedure. These were the two-package polyurethane (clear rubbery) and the photo-curable (clear film plastic) systems. Other adhesives are contemplated.

All literature and publications referred to and described herein are incorporated herein in their entirety.

We claim:

1. A swab constructed to collect and release a biological sample comprising a liquid, said swab comprising an applicator and sea-island bicomponent fibers, wherein at least about 85% of the fibers comprise randomly splayed terminal ends of the islands of said bicomponent fibers along a length of about 50% or less from said ends.

2. The swab of claim 1 wherein said bicomponent fibers comprise a first polyester sea material and a second polyester island material.

3. The swab of claim 2 wherein said first polyester has a lower melting point than said second polyester.

4. The swab of claim 2 wherein said first polyester has a greater solubility in alkaline solution than said second polyester.

5. The swab of claim 4 wherein the first polyester has a greater solubility in alkaline solution of sodium hydroxide, as compared to the second polyester.

6. The swab of claim 5 wherein the first polyester has greater solubility in an alkaline solution of sodium hydroxide solution containing about 5% to about 50% by weight sodium hydroxide in water, as compared to the second polyester.

7. The swab of claim 6 wherein the first polyester has greater solubility in an alkaline solution of about 10% by weight sodium hydroxide in water, as compared to the second polyester.

8. The swab of claim 4 wherein the first polyester has greater solubility in a heated alkaline solution as compared to the second polyester.

9. The swab of claim 8 wherein the first polyester has greater solubility in an alkaline solution heated to a temperature of about 170° F. to about 190° F. as compared to the second polyester.

10. The swab of claim 1 wherein the fibers are attached to an end portion of said applicator.

11. The swab of claim 10 wherein said fibers are adhered to said end portion with an adhesive.

12. The swab of claim 11 wherein said adhesive is selected from the group consisting of a photocurable acrylic adhesive and a polyurethane adhesive.

13. The swab of claim 1 wherein said bicomponent fibers comprise a polyethylene terephthalate sea material and a polyamide island material.

14. The swab of claim 1 wherein said bicomponent fibers comprise 10-3000 island parts per fiber.

15. The swab of claim 14 wherein said fibers comprise 10-240 island parts per fiber.

16. The swab of claim 14 wherein said fibers comprise 10-64 island parts per fiber.

17. The swab of claim 14 wherein said fibers comprise 10-37 island parts per fiber.

18. The swab of claim 14 wherein said fibers comprise 10-36 island parts per fiber.

19. The swab of claim 14 wherein said fibers comprise 10-24 island parts per fiber.

20. The swab of claim 14 wherein said fibers comprise 24-36 island parts per fiber.

21. A method of forming the swab of claim 10 comprising adhering the bicomponent fibers to said applicator, removing a portion of the sea component of said bicomponent fibers in a heated alkaline solvent, and forming said randomly splayed fibers by application of mechanical force to the ends of said fibers which have had said sea component removed.

22. A method of collecting a biological sample comprising contacting the swab of claim 1 with a source of biological material such that a sample of the material is retained by the swab.

* * * * *